(12) United States Patent
Bates et al.

(10) Patent No.: US 8,298,173 B2
(45) Date of Patent: Oct. 30, 2012

(54) PARTICLE CASSETTES

(76) Inventors: Nigel Robert Bates, Oxford (GB); Philip Thomas Price, Oxford (GB); John Watson, Oxon (GB); Stuart Graham Weekes, Oxon (GB)

( * ) Notice: Subject to any disclaimer, the term of this patent is extended or adjusted under 35 U.S.C. 154(b) by 374 days.

(21) Appl. No.: 12/303,885

(22) PCT Filed: Jun. 4, 2007

(86) PCT No.: PCT/GB2007/002047
§ 371 (c)(1), (2), (4) Date: Jul. 1, 2010

(87) PCT Pub. No.: WO2007/141501
PCT Pub. Date: Dec. 13, 2007

(65) Prior Publication Data
US 2010/0298767 A1    Nov. 25, 2010

(30) Foreign Application Priority Data
Jun. 9, 2006 (GB) .................................. 0611443.3

(51) Int. Cl.
*A61M 5/30* (2006.01)
*B23P 11/00* (2006.01)
(52) U.S. Cl. ............. 604/72; 604/206; 206/438; 29/428
(58) Field of Classification Search .................. 604/72, 604/206, 533; 156/60–61; 206/364, 438; 29/428
See application file for complete search history.

(56) References Cited

U.S. PATENT DOCUMENTS

| 5,630,796 | A | 5/1997 | Bellhouse et al. | 604/49 |
| 8,061,006 | B2 * | 11/2011 | Kendall et al. | 29/450 |
| 2003/0019558 | A1 | 1/2003 | Smith et al. | 156/61 |
| 2004/0255447 | A1 * | 12/2004 | Kendall et al. | 29/428 |
| 2006/0243142 | A1 * | 11/2006 | Mullins et al. | 100/3 |
| 2008/0300535 | A1 * | 12/2008 | Kendall et al. | 604/72 |
| 2008/0315444 | A1 * | 12/2008 | Skipper | 264/1.38 |

FOREIGN PATENT DOCUMENTS

| DE | 1942023 | 4/1966 |
| EP | 0934754 | 8/1999 |
| GB | 1296851 | 11/1972 |
| WO | WO 9424263 | 10/1994 |
| WO | WO 03011379 | 2/2003 |
| WO | WO 03099985 | 12/2003 |

* cited by examiner

*Primary Examiner* — Quynh-Nhu H Vu
(74) *Attorney, Agent, or Firm* — Matthew J. Pugmire

(57) ABSTRACT

A method of producing a particle cassette for a needleless syringe device which alleviates problems of providing a chamber for the confinement of particles which is hermetically sealed from the environment. A predetermined force is applied in the longitudinal direction to push first and second cassette parts together so as to cause plastic deformation of a portion of the first cassette part so as to create said hermetically sealed chamber. The cassette parts are preferably made of PETG and have bonded thereto rupturable membranes preferably made of PET. The sealing is preferably achieved at the end of a protrusion on the first cassette part which is tapered and which interacts with the membrane of the second cassette part.

20 Claims, 5 Drawing Sheets

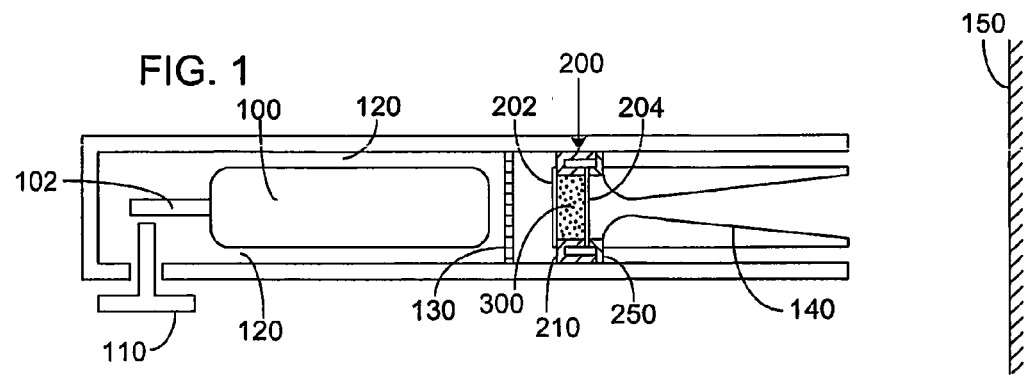
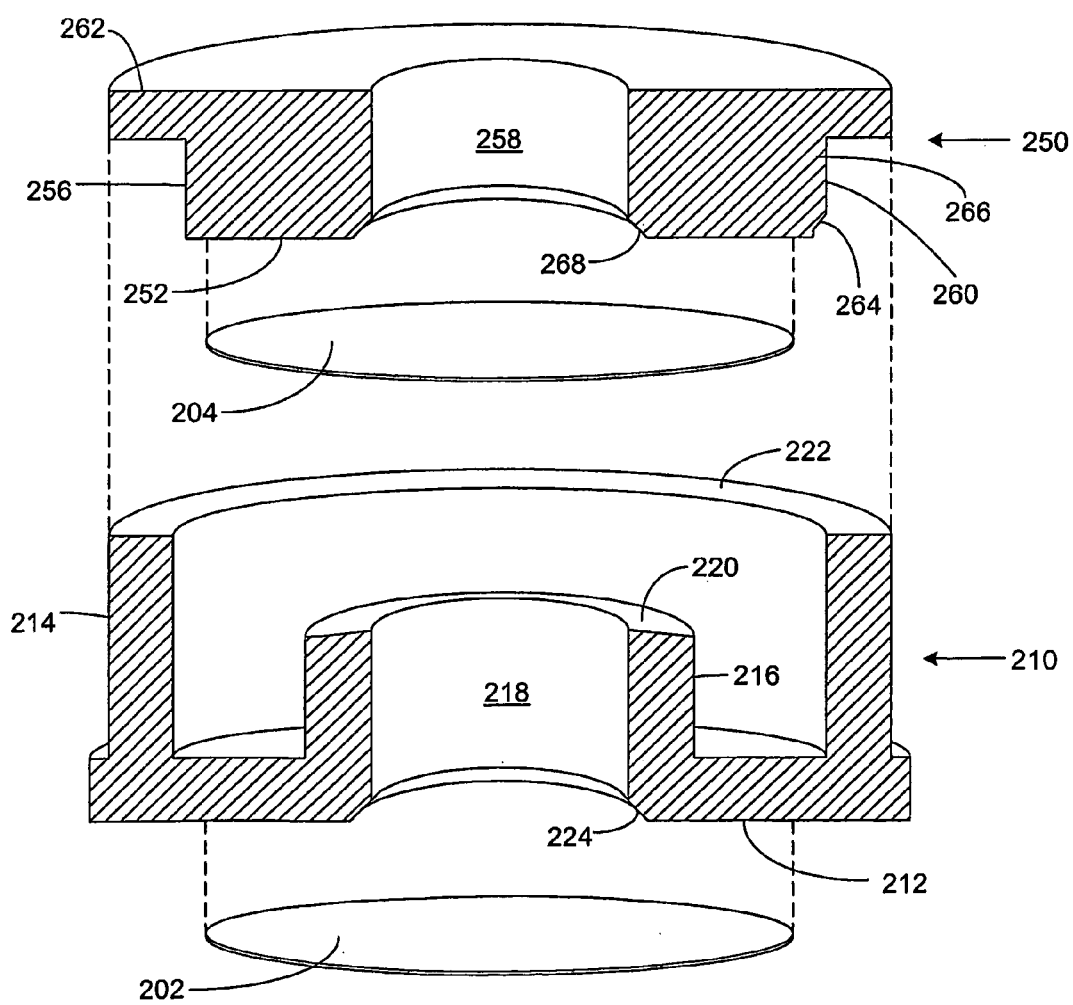

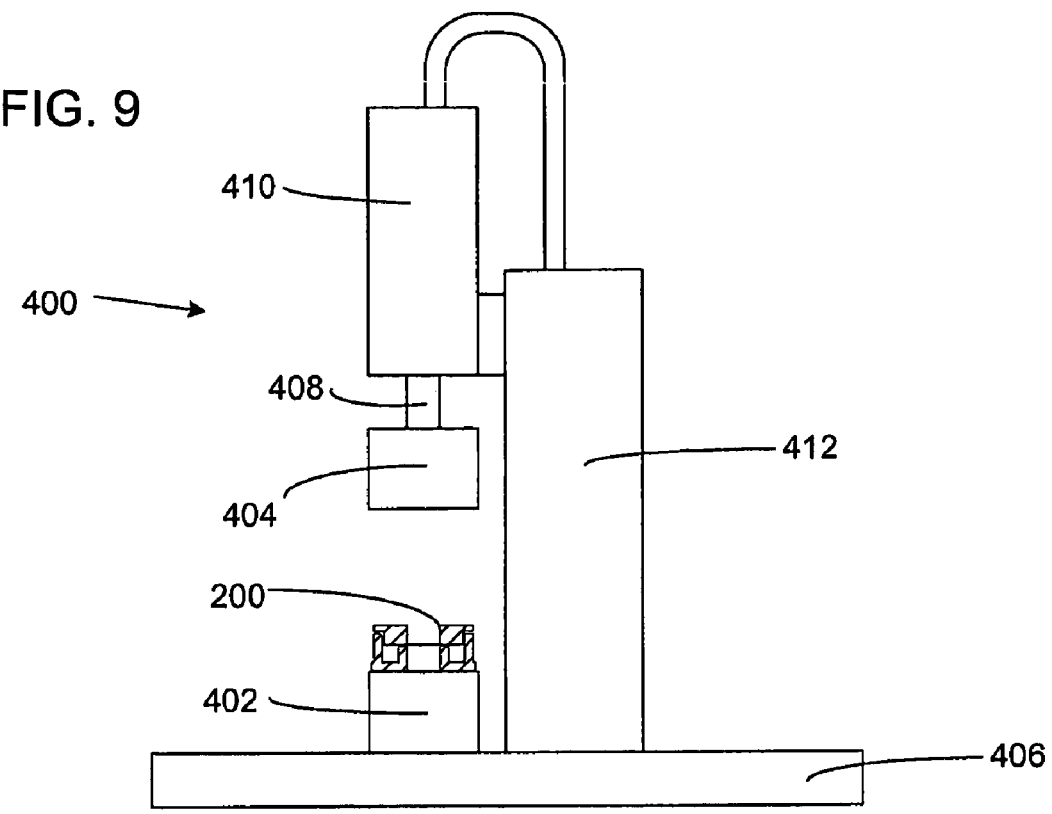
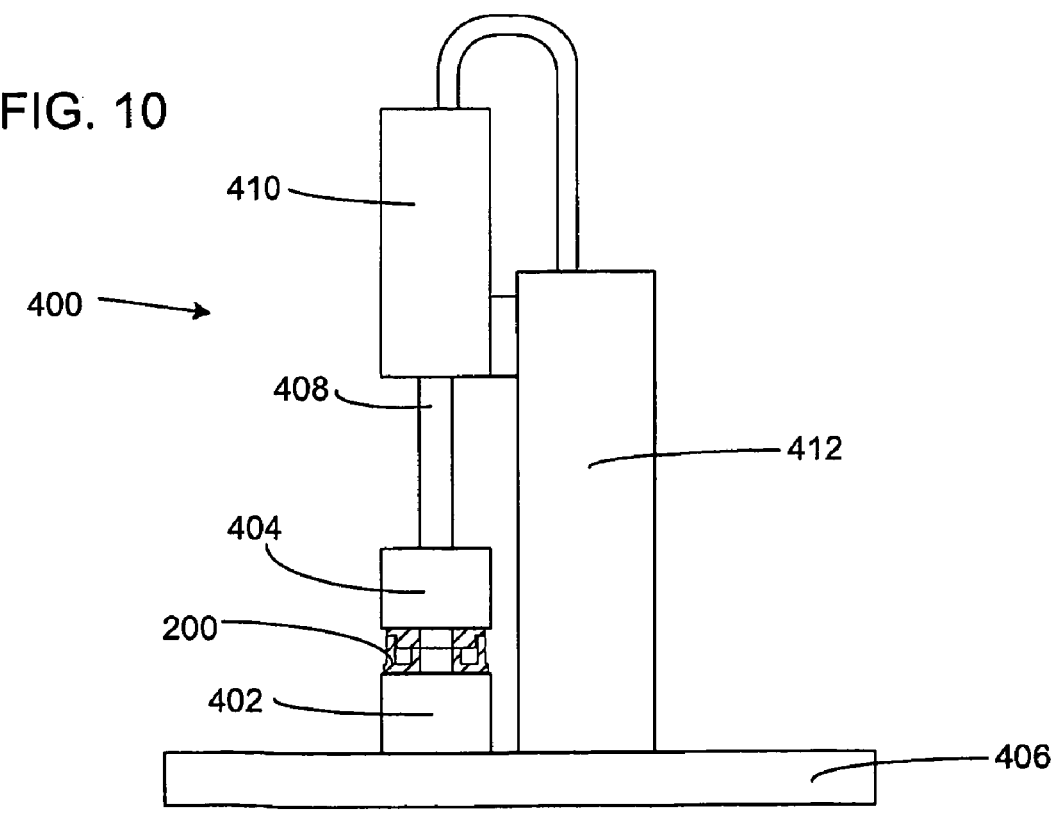

PARTICLE CASSETTES

The present application claims priority from Great Britain Patent Application No. 0611443.3, filed on Jun. 9, 2006 and International Application No. PCT/GB2007/002047, filed on Jun. 4, 2007, all of which are incorporated by reference herein for all purposes.

TECHNICAL FIELD OF THE INVENTION

The present invention relates generally to the retention of particles prior to the needleless injection of those particles in a gas stream. More specifically, the present invention relates to particle cassettes having a pair of membranes which retain the particles in a chamber therebetween and to methods of manufacturing and assembling such particle cassettes.

BACKGROUND OF THE INVENTION

Needleless syringe devices are known from WO 94/24263. In this document, a needleless syringe is disclosed which entrains particles in a gas stream accelerated through a nozzle so that the particles may be injected into a target, such as human skin or other cells. For many applications, there is a need for the particles to be maintained in a sterile environment prior to actuation of the device. WO 94/24263 discloses for this purpose a particle cassette comprising a central annular ring having rupturable membranes bonded to each face so as to form a self contained sealed unit containing the particles to be injected. Upon actuation of the device, the membranes rupture allowing the particles initially contained between the membranes to be entrained in the gas flow and then delivered into the target. WO 94/24263 is hereby incorporated by reference.

An improvement to the particle cassette of WO 94/24263 is disclosed in WO 03/011379. In this document, a particle cassette comprised of two parts, each part having bonded thereto a rupturable membrane, is disclosed. In the preferred mode of manufacture, the membranes are heat-bonded to their respective cassette parts and the particle cassette is formed by bringing the cassette parts together so as to create a chamber for the particles. This overcomes the problem with the WO 94/24263 particle cassette that heat-bonding the second membrane to the annular ring can cause degradation of the particles in the chamber. WO 03/011379 is also hereby incorporated by reference.

FIG. 13 of WO 03/011379 shows a particle cassette having a first cassette part 70 with a membrane 71 heat-bonded thereto and a second cassette part 72 with a membrane 73 heat-bonded thereto. The first and second cassette parts are brought together in the longitudinal direction such that ribs on the external surface of the second cassette part interact with the inside annular surface 78 of a protrusion on a first cassette part. This provides an interference fit which holds the first and second cassette parts together. The particle cassette is designed to be assembled by hand.

A problem with such hand assembly is that the chamber 77 for the confinement of particles is not hermetically sealed. This has been confirmed by subjecting the particle cassette of FIG. 13 of WO 03/011379 to vacuum tests whereby it becomes evident that although the chamber 77 is sealed to the extent that the particles cannot escape, it is still possible for gases and even smaller particles (e.g. microbes) to infiltrate into the chamber 77. Accordingly, the present invention seeks to alleviate this problem.

SUMMARY OF THE INVENTION

The present invention addresses the above-mentioned problem by providing a method of producing a particle cassette, apparatus for producing a particle cassette, a kit of parts which, when assembled, forms a particles cassette, a particle cassette and first and second cassette parts which allow a properly hermetically sealed particle confinement chamber to be created.

In accordance with the first aspect of the invention there is provided a method of producing a particle cassette for a needleless syringe device, said method comprising the steps of: (a) providing a first cassette part having a first rupturable membrane bonded thereto; (b) providing a second cassette part having a second rupturable membrane bonded thereto; (c) aligning said first and second parts longitudinally; (d) applying a predetermined force in the longitudinal direction so as to push the first and second cassette parts together to cause plastic deformation of a part of said cassette so as to create a hermetically sealed chamber between said first rupturable membrane and said second rupturable membrane.

It has been found that applying a predetermined force sufficient to cause plastic deformation of a portion of the cassette creates a cold formed seal between the components of the particle cassette that can thereafter withstand the vacuum tests sufficient to prove hermetic sealing of the chamber. The use of a predetermined force, rather than an irregular and non-repeatable force achieved by hand, ensures that particle cassettes produced using the method of the first aspect are sealed to a known level of confidence, meaning that each particle cassette so produced does not necessarily have to be tested for hermetic sealing. The provision of a hermetically sealed chamber gives confidence that any products using the particle cassette are free from the possibility of contamination of the particles.

Furthermore, the advantages of WO 03/011379 in that the particles are not degraded due to a heat-bonding process are retained.

Preferably, the plastic deformation occurs at a predetermined portion of the first cassette part such as a sealing end face. This allows the manufacturing process to be made repeatable and helps to guarantee that hermetic sealing will occur upon application of the predetermined force.

The sealing end face preferably has a tapered shape prior to assembly. The use of such a taper means that a relatively small surface area for the sealing end face is initially in contact with the second cassette part. As plastic deformation occurs, the tapered surface flattens out so as to conform to the shape of the corresponding portion of the second cassette part and the surface area of contact thereby increases. The mode of plastic deformation and the increase in contact surface area helps to cause a cold formed seal whereby the first and second cassette parts are sealed together to create the hermetic chamber for the confinement of particles.

Ensuring that the sealing end face is sealed directly against the second rupturable membrane of the second cassette part gives an additional advantage in that sealing between the second cassette part and the second rupturable membrane is thereby reinforced. The second rupturable membrane is effectively "sandwiched" between the first and second cassette parts and the predetermined force helps to improve sealing on both sides of the second rupturable membrane. Also, the second rupturable membrane can be made of a different material to the first cassette part to ensure that the first cassette part deforms rather than the second rupturable membrane.

The sealing end face of the first cassette part is preferably located on an annular protrusion of the first cassette part. This enables the plastic deformation of the first cassette part to be controlled and allows the provision of a known and predetermined sealing area that cannot exceed the size of the sealing end face located on the annular protrusion.

The particles for confinement in the chamber are preferably introduced between steps (b) and (c). This can most readily be achieved by laying the first cassette part horizontally with its sealed membrane facing downwards, positioning the particles on the sealed membrane and vertically lowering the second cassette part onto the first cassette part.

Such vertical lowering is preferably achieved using a pair of platens that compress the cassette parts towards one another. Such compression is preferably such as to move the cassette parts towards one another longitudinally during assembly.

The predetermined force applied is preferably chosen so as to create a sealing pressure that exceeds the compressive yield strength of the first cassette part.

A range of materials may be used for the first cassette part and/or the second cassette part. Particularly preferred is copolyester (PETG). Particularly preferred for the rupturable membrane is polyethylene terephthalate (PET). The fact that PET has a slightly higher compressive yield strength than PETG means that the first cassette part plastically deforms when the sealing end face is pushed up against the second rupturable membrane.

The predetermined force used to seal the cassette parts together is preferably such as to cause a sealing area that is at least 10% of the maximum possible sealing area available. The maximum possible sealing area available in the case that the sealing end face lies on a protrusion will be the area of the end face of the protrusion. This requirement can be expressed as:

$$F \geq 0.1 C A_{max}$$

wherein F is the predetermined force in Newtons, C is the compressive yield strength of the portion of the first cassette part that plastically deforms in MPa and $A_{max}$ is the maximum possible sealing area achievable with the cassette parts in $mm^2$.

The predetermined force is also advantageously given by:

$$F \geq 2C$$

The predetermined force is preferably greater than 200 N, more preferably greater than 500 N, more preferably greater than 800 N and more preferably still greater than 1000 N. Values of about 1200 N and about 1800 N have also been tested and have been found to be acceptable.

The predetermined force is preferably held for a predetermined period of dwell time. This period is ideally 0.1 to 15 seconds, advantageously 1 to 10 seconds and more preferably 3 to 7 seconds. A predetermined force of 1500 N or more together with a hold time of 3.5 seconds or more has been found to produce a very reliable particle cassette.

In a second aspect of the invention there is provided apparatus for producing a particle cassette for a needleless syringe, said apparatus comprising: a first platen for supporting a first cassette part thereon; a second platen separated from said first platen by a distance sufficient to allow a second cassette part to be placed on and aligned with said supported first cassette part; driving apparatus to move said platens together so as to compress said particle cassette parts therebetween and apply a predetermined force to said cassette parts for a predetermined dwell time so as to produce a particle cassette having a hermetically sealed chamber for the confinement of particles.

One preferred mechanism for driving the platens together is to use a source of compressed gas which is preferably regulated so as to supply a predetermined pressure and thereby produce the predetermined force.

The use of platens allows the predetermined force to be transmitted reliably to the first and second cassette parts such that the sealing mechanism can reliably be achieved at the point of contact between the cassette parts.

According to a third aspect of the invention there is provided a kit of parts for use in the manufacture of a particle cassette for a needleless syringe device, said kit comprising: a first cassette part; a second cassette part having a rupturable membrane bonded thereto; wherein said first cassette part comprises a first protrusion in the longitudinal direction arranged to interact, during assembly, with said second cassette part so as to help hold said first and second cassette parts together; said first cassette part further comprising a second protrusion inward of said first protrusion, said second protrusion comprising a sealing end face for sealing against the second particle cassette part when assembled.

According to a fourth aspect of the invention there is provided a first cassette part of a particle cassette for a needleless syringe device, said first cassette part designed to interact with a second cassette part to create a chamber for the confinement of particles, said first cassette part comprising: a first protrusion in the longitudinal direction arranged to interact with said second cassette part so as to help hold said first and second cassette parts together; and a second protrusion inward of said first protrusion, said second protrusion comprising a sealing end face for sealing against the second particle cassette part According to a fifth aspect of the invention there is provided a first cassette part of a particle cassette for a needleless syringe device, said first cassette part designed to interact with a second cassette part to create a chamber for the confinement of particles, wherein said first cassette part is made of PETG.

According to a sixth aspect of the invention there is provided a second cassette part of a particle cassette for a needleless syringe device, said second cassette part designed to interact with a first cassette part to create a chamber for the confinement of particles, said second cassette part having a rupturable membrane of PET sealed thereto.

BRIEF DESCRIPTION OF THE DRAWINGS

Embodiments of the present invention will now be described, by way of example only, with reference to the accompanying schematic drawings, in which:

FIG. 1 shows a needleless syringe device typical of the type which are able to utilise the particle cassette manufactured according to the present invention;

FIG. 2 shows an exploded view of the particle cassette of the preferred embodiment of the present invention;

FIG. 9 shows apparatus for producing a particle cassette according to the present invention in the initial position; and FIG. 10 shows the apparatus of FIG. 7 but with the platens compressed together.

DESCRIPTION OF PREFERRED EMBODIMENTS

Figure 3:
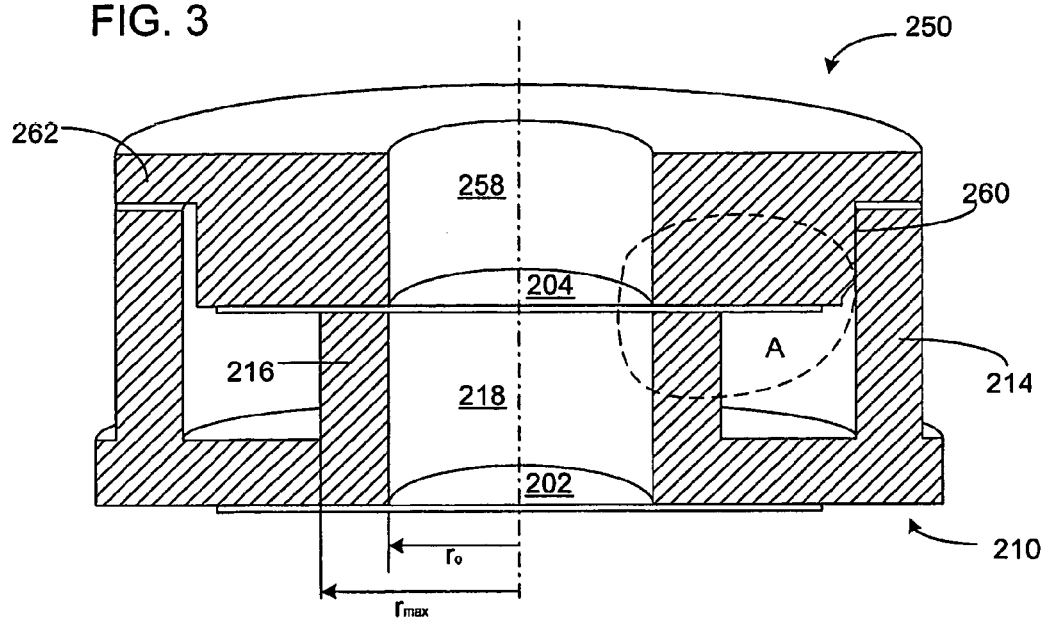
FIG. 3 shows the particle cassette of FIG. 2 in the assembled condition.

In the drawings components are not necessarily drawn to scale. The drawings are schematic for reasons of clarity. In reality the thickness of the rupturable membranes may be much less than is shown and/or the volume of particles may be so small as to be barely visible to the naked eye.

FIG. 1 shows a needleless syringe device which can accept and utilise the particle cassette of the present invention. The needleless syringe comprises a reservoir 100 of compressed gas, typically helium at super-atmospheric pressure of, for example 20 to 60 bar. The reservoir 100 is in the form of a bulb having a frangible tip 102. An actuation button 110 is provided at one end of the device and is positioned such that depressing the button causes it to bear against the frangible tip 102 so as to break the frangible tip 102 of the reservoir 100. Gas at super-atmospheric pressure is thus released from the reservoir 100 and flows around the outside of reservoir 100 down the passages 120, in the manner described in EP 0,934,754. The gas passes through a filter 130 before reaching the particle cassette generally designated as 200. The particle cassette comprises a first cassette part 210 having a first rupturable membrane 202 bonded thereto and a second cassette part 250 having a second rupturable membrane 204 bonded thereto. Particles 300 are located in the chamber between the membranes. The pressure of the gas released from the reservoir causes the membranes 202, 204 to successively burst such that the particles 300 are entrained in a gas stream. The gas stream (containing the particles) is accelerated in a nozzle 140, preferably of convergent-divergent configuration towards a target 150. The target 150 is preferably skin or other tissue of a living human or animal. It will be appreciated that this description of syringe is merely exemplary and modifications may be made in accordance with the teachings of the prior art concerning such needleless syringes. For example, the reservoir 100 may comprise a valve rather than a frangible tip and may be positioned such that gas flows directly out and towards the filter rather than having to turn 180° upon exiting the reservoir. Further, a silencing system and a spacer for spacing the nozzle exit from the target may be provided as is known in the art. The particle cassette of the present invention is generally applicable to any type of needleless syringe in which particles are picked up and entrained in a gas flow.

It will be appreciated that the downstream membrane 204 is, prior to actuation of the syringe, open to the atmosphere via the opening of the nozzle 140. To ensure that the particles are hermetically sealed from the atmosphere prior to use of the syringe, the present invention provides that no gases in the atmosphere can infiltrate between the cassette parts 210, 250 to the space where the particles 300 are located.

The construction of the cassette parts is shown in FIG. 2. This Figure shows the cassette parts cut along a diameter with cross-hatching representing the cut plane. The rupturable membranes 202, 204 are not shown cut. The first cassette part 210 has a base surface 212 to which the membrane 202 is bonded, preferably by heat-bonding. The heat-bonding procedure ensures a hermetic seal between the membrane 202 and the first cassette part 210.

The first cassette part 210 comprises a first annular protrusion 214 extending around the outermost periphery of the first cassette part 210. The purpose of this protrusion is to interact with corresponding features of the second cassette part 250 so as to keep the two cassette parts together. The first annular protrusion 214 has at its end a ring-shaped face 222. A second annular protrusion 216 is provided radially inwardly of the first annular protrusion 214. This annular protrusion 216 surrounds and defines the particle confinement chamber 218 of the assembled particle cassette. The second annular protrusion 216 has at its end a ring-shaped sealing face 220. This sealing face 220 is designed to seal against the second rupturable membrane 204 when the particle cassette is assembled. As shown in FIG. 2, the sealing face 220 is tapered such that the face is closer to the rupturable membrane 204 at its radial innermost extent than it is at its radial outermost extent. The taper may be provided in the other direction to achieve the same effect. The taper is preferably very shallow, for example 5° from the plane perpendicular to the longitudinal direction (i.e. the plane of the membranes 202 and 204). The taper is designed to be very shallow so that the sealed surface area increases relatively quickly as the two cassette parts are moved closer together to allow a larger seal area to be obtained with quite small longitudinal displacements of the cassette parts. Other values for the taper such as 10° and 15° may equally be used.

The first cassette part 210 preferably has a filleted edge at the section which interacts with the first rupturable membrane 202. This fillet 224 provides an area where excess material can flow that is created during the heat-bonding procedure. This prevents material extending outwardly of the inner radius of the particle confinement chamber 218 and helps to ensure repeatable and desirable bursting characteristics for the membrane 202 during use.

The second cassette part 250 comprises a base surface 252 to which the second rupturable membrane 204 is bonded, preferably heat-bonded. Such heat-bonding creates a hermetic seal between the second cassette part 250 and the second rupturable membrane 204. The second cassette part 250 comprises an annular portion 256 which defines a passage 258 at its radially inward extent and defines a mating surface 260 at its radially outer extent. The passage 258 allows the gas and entrained particles to flow out of the particle cassette during use and the radially outer-most face 260 preferably interacts with the first annular protrusion 214 of the first cassette part so as to hold the cassette together. The radially outermost face 260 is the outer face of a series of castellations surrounding the perimeter of the second cassette part 250. As shown in FIG. 2, these castellations have a tapered entry section which assists in the alignment of the first and second cassette parts. The reason for using castellations is to allow air to escape from between the cassette parts as they are brought together.

The second cassette part 250 also has a flange portion 262 which extends radially outwardly of the annular portion 256. The flange portion 262 can be designed to limit the possible relative movement between the first and second cassette parts as they are brought together in the longitudinal direction. In particular, the cassette parts can be brought together no closer once the flange portion 262 comes into contact with the face 222 of the first annular protrusion 214 of the first cassette part.

The second cassette part 250, like the first cassette part 210, has a fillet 268 at the edge of the inner circumference that interacts with the rupturable membrane 204. Again, this provides space for material to flow into during the heat-bonding process.

The particle cassette manufacturing process starts with bonding the membrane 202 to the base surface 212 of the first cassette part 210 and bonding the membrane 204 to the base surface 252 of the second cassette part 250. These bonds are preferably heat bonds which have been found to provide a good hermetic barrier. However, other types of bonding such as gluing may be used. The unassembled cassette parts are then preferably irradiated so as to sterilise them, preferably with gamma radiation. The parts are then brought together as will be explained further.

FIG. 3 shows the cassette in its assembled condition. The first and second cassette parts are aligned longitudinally as shown in FIG. 2 and pressed together to achieve the condition of FIG. 3. The initial taper 264 of the rib 266 helps to longitudinally align the cassette parts even if they are initially brought together not in exact alignment. The force used to press the parts together is such as to press the second rupturable membrane 204 against the tapered sealing end face 220 of the first cassette part 210. The force is sufficient to cause plastic deformation of the sealing end face 220 of the second annular protrusion 216 and, in the example of FIG. 3, the force has been sufficient to cause complete flattening of the end face 220. The plastic deformation of the end face 220 causes a hermetic seal between the first cassette part 210 and the second rupturable membrane 204. Thus, the chamber for the confinement of particles 218 is completely sealed from the environment.

It is preferable to provide means for holding the particle cassette together and this is conveniently achieved by allowing for interaction between the outer surface 260 of ribs 266 of the second cassette part 250 with the inner surface of the first annular protrusion 214 of the first cassette part 210. The one or more ribs 266 may be located either on the outer surface of the second cassette part (as shown in FIGS. 2 and 3) or on the inner surface of the first annular protrusion 214 such that an interference fit or friction fit is directly provided between the first and second cassette parts. The ribs are preferably located on the outer surface 260 of the second cassette part but can just as easily be provided on the inner surface of the first annular protrusion 214 of the first cassette part 210. The interaction between the first and second cassette parts is preferably achieved using ribs 266 such that, at certain circumferential locations, air gaps exist which allow the escape of air from between the cassette parts as the two parts are brought together. The ribs can be similar to the ribs 74 shown in FIG. 13 of WO 03/011379. The outer diameter of the surface 260 is preferable slightly larger than the inner diameter of the inner surface of the protrusion 214. This causes a hoop-stress to be set up in the region of the protrusion of the first cassette part 210 such that there is an interference fit between the two cassette parts.

The flange 262 of the second cassette part 250 can, if desired, act as a stopping member to prevent relative displacement between the first and second cassette parts once the flange 262 comes into contact with the end face 222 of the first annular protrusion 214.

The procedure of bringing the cassette parts together, and of establishing a seal using the cold-forming process will be described with reference to FIGS. 4a to 4d.

Figure 4A:
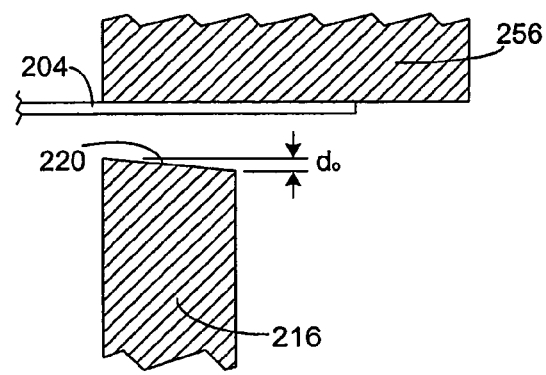
FIGS. 4a to 4d show stages in the assembly of the particle cassette.
Figure 4B:
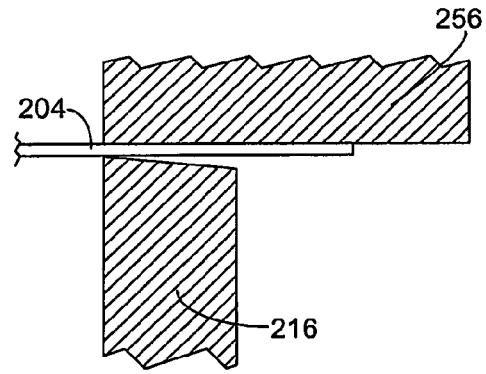

FIGS. 4a to 4d show a close-up of the region outlined in dashed lines and identified as "A" in FIG. 3. Initially, the first cassette part 210 is located on a horizontal surface, such as a platen, with its membrane 202 facing downwards and the chamber 218 open to the atmosphere. The particles may at this stage be provided to the chamber 218. The second cassette part 250 is then aligned with the first cassette part longitudinally and this is shown in FIG. 4a. Due to the ribs 266 on the outer annular surface 260 of the second cassette part, which preferably have a tapered front surface to aid in alignment (see also ribs 74 of WO 03/011379), the membrane 204 will initially be held some way above the sealing face 220 as the ribs prevent automatic insertion via gravity of the second cassette part 250 into the gap defined inside of the first annular protrusion 214 of the first cassette part 210. As pressure is applied to the second cassette part 250, preferably by a second platen which compresses the first and second cassette parts towards one another, the second cassette part 250 and its attached membrane 204 move downwardly until the membrane 204 comes into contact with the sealing face 220 of the second annular protrusion 216 of the first cassette part 210. Due to the tapered shape of the second annular protrusion 216, the membrane 204 comes into contact with the inner part of the sealing face only, as shown in FIG. 4b. At this point, there will be a very small area over which the membrane 204 is in contact with the sealing face 220. At this point the first and second cassette parts are preferably quite strongly held together by the interference-type interaction between face 260 and first protrusion 214 (e.g. via ribs).

Figure 4C:
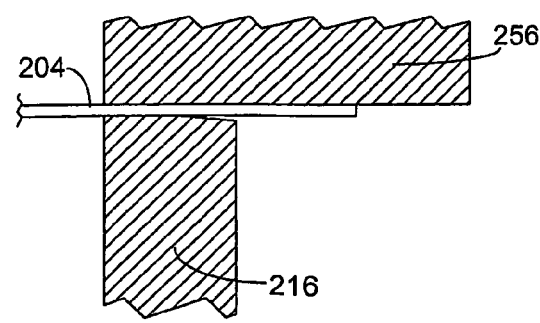
Figure 4D:
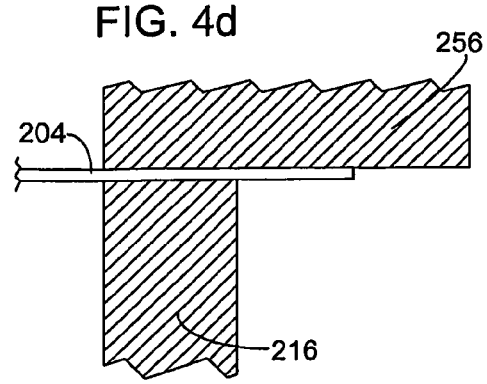

As the predetermined force is applied to the cassette parts, the pressure at the point of contact between the membrane 204 and the sealing face 220 will cause the sealing face 220 to plastically deform so as to move from a tapered configuration to a flatter configuration, as shown in FIG. 4c. This in turn will increase the area of contact between the sealing face 220 and the membrane 204. As the force used is predetermined and fixed, the increase in area will cause a decrease in pressure at the contact point. The end face 220 will continue to plastically deform until the pressure achieved over the contact area is less than the compressive yield strength of the material at the sealing end face 220. FIG. 4d shows the situation whereby a predetermined force has been used such that the pressure always exceeds the compressive yield strength of the sealing end face 220 of the second annular protrusion 216. In this case, the first and second cassette parts will, if unhindered, continue to move closer together until the flange 262 of the second cassette part 250 comes into abutment with the end face 222 of first annular protrusion 214 of the first cassette part 210.

It is not necessary for the entire sealing end face 220 to be flattened in the manner shown in FIG. 4d. The procedure of creating a hermetic seal can be equally carried out by stopping at some intermediate point as shown in FIG. 4c whereby the end face 220 is only partially flattened. This can be achieved by selecting a predetermined force which is not sufficient to cause yielding of the second annular protrusion 216 across its whole area. In other words, the force is selected such that, with the area of contact shown in FIG. 4c, the compressive yield strength of the material is no longer achieved. In general, the material of the second annular protrusion 216 will stop plastically deforming once the pressure at the sealing end face 220 falls just below the compressive yield strength of the material.

In order to achieve consistent hermetic sealing, it has been found to be desirable to hold the predetermined force for a certain period of dwell time. This period of time preferably ranges from 0.1 to 10 seconds, more preferably 1 to 7 seconds, more preferably still 2 to 4 seconds. It is believed that this holding dwell time is helpful in ensuring that the plastic deformation has time to take place and to create a cold formed seal.

Figure 5:
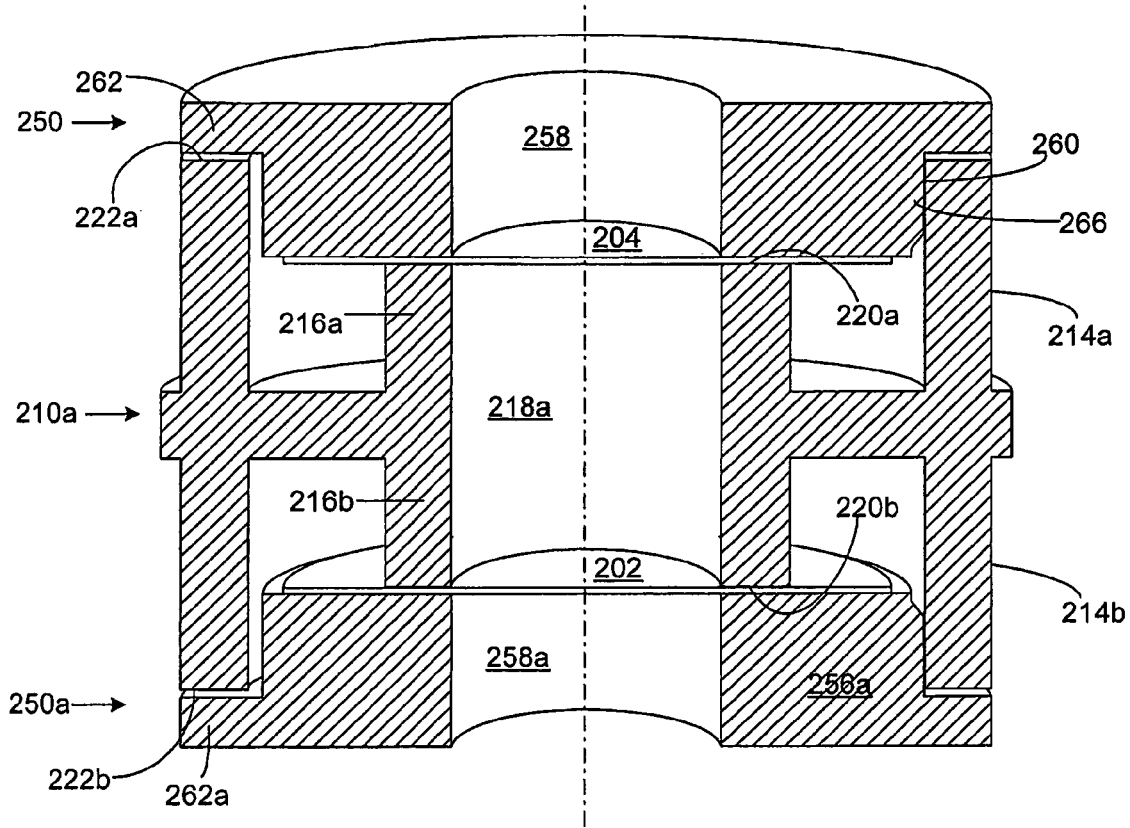
FIG. 5 shows a second embodiment of particle cassette.

FIG. 5 shows a second embodiment of particle cassette. This embodiment has three cassette parts, first cassette part 210a, second cassette part 250 and third cassette part 250a. In this embodiment, the third cassette part 250a is identical to the second cassette part 250. The parts of the first cassette part 210a that interact with the second and third cassette parts are also identical to the corresponding parts of the first cassette part 210 in the first embodiment. As in the first embodiment, the second cassette part 250 has an outer flange 262, an annular portion 256 which defines a passage 258 at its radially inward extent and a series of ribs 266 around the outer periphery of the annular portion 256. A second rupturable membrane 204 is heat-bonded to one face of the second cassette part 250 as shown in FIG. 5. The third cassette part 250a has an identical construction to the second cassette part 250 and so further description will be avoided for the sake of simplicity.

The first cassette part 210a has a first annular protrusion 222a for interacting with the second cassette part 250 and, symmetrical therewith, a second protrusion 222b for interacting with the third cassette part 250a. Inwardly of the first protrusions are second protrusions 216a and 216b, also symmetrically arranged, for interaction with the second and third cassette parts respectively. A chamber for the confinement of particles 218a is provided similar to the first embodiment.

It will be appreciated that the first cassette part 210a of the second embodiment does not have any rupturable membranes bonded to it. It will also be appreciated that the plastic deformation occurs at two positions in the first cassette part 210a; at the sealing face 220a and also at the sealing face 220b.

Figure 6:
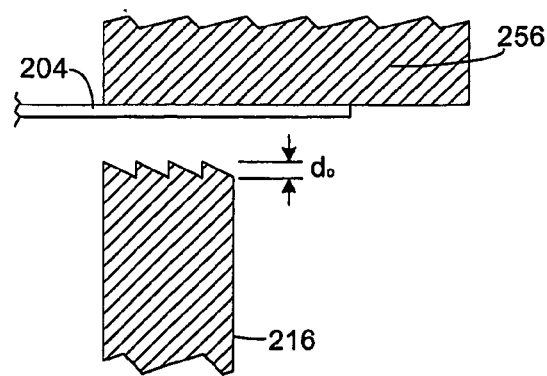
FIG. 6 shows an alternative arrangement for the sealing end face.

FIG. 6 shows an alternative arrangement for the sealing end face that may be applied to either the first or second embodiment. Here, instead of a single taper 220 which spans the length of the sealing end face, a series of saw-tooth tapers are provided. This allows the taper to have a greater angle thereby accelerating the rate at which a seal area will be formed upon displacement of the cassette parts towards one another.

The forces, pressures, displacement and sealing areas can be represented in terms of mathematical equations. At the position of FIGS. 4b, 4c and 4d, the pressure over the area of contact will be equal to the force provided divided by the contact area. This can be represented by the well-known equation $$P = \frac{F}{A} \quad (1)$$

where pressure P is measured in MPa, force F is measured in Newtons and area A is measured in mm². The force F can thereby be selected so as to achieve a minimum area of sealing. If the pressure P is selected to be the compressive yield strength C of the material of the second annular protrusion 216 and the area A is selected to be the minimum sealing area $A_{min}$, rearranging Equation 1 gives:

$$F = CA_{min} \quad (2)$$

As an example, if a minimum sealing area $A_{min}$ of 10 mm² is desired and the material for the second annular protrusion 216 is PETG (compressive yield strength C approximately 85 MPa), then the predetermined force required will be 85×10=850 N.

The relationship between the sealing area at any point in time and the displacement of the second cassette part relative to the first cassette part can also be calculated. If the position of FIG. 4b whereby the membrane 204 only just touches the inside edge of the second annular protrusion 216 is taken as the point of zero displacement, and further displacement such as to bring the two cassette parts together is considered to be positive displacement, then it can be shown that the sealing area at the general position shown on FIG. 4c whereby the cassette parts have moved together by a distance d can be expressed as follows:

$$A = \pi\left(\left(\frac{d}{d_0}(r_{max} - r_0)\right)^2 + \frac{2dr_0}{d_0}(r_{max} - r_0)\right) \quad (3)$$

where A is the instantaneous sealing area, d is the instantaneous cassette part displacement, $d_0$ is the displacement when the taper has been completely flattened (see FIG. 4a), $r_{max}$ is the outer radius of the protrusion 216 and $r_0$ is the inner radius of the protrusion 216.

This Equation is plotted in FIG. 5 for the case when $d_0$=0.1 mm, $r_{max}$=4.2 mm and $r_0$=3 mm. It can be seen from FIG. 5 that the sealed area A increases with the square of the displacement d although the curve is such that, over the range of interest, the correlation is nearly linear.

In this example, the maximum sealing area is the total area of the end face 220. This can be calculated by making d in Equation 3 equal to the difference in longitudinal height between the inner edge of the sealing area 220 and the outer edge of the sealing area 220. This is given by the value $d_0$, which is 0.1 mm in the present example. From Equation 3, the sealing area when d=$d_0$, $r_{max}$=4.2 mm and $r_0$=3 mm is $A_{max}$=27.14 mm². Preferably, the force is selected such that the sealing area is at least 10% of the maximum sealing area available. This can be represented by the equation:

$$F \geq 0.1 CA_{max} \quad (4)$$

where F is the predetermined force, C is the compressive yield stress of the material at the sealing end face 220 and $A_{max}$ is the maximum possible sealing area achievable (27.14 mm² in the example of FIGS. 5 and 6).

The sealing effectiveness is thought to be proportional to the seal area and so, with the embodiments of the present invention in which a tapered sealing face 220 is utilised, the sealing area achieved can be guaranteed by providing for a certain displacement between the first and second cassette parts. The amount of displacement that is possible can be adjusted by adjusting the dimensions of the flange 262 and the first annular protrusion 214. A certain predetermined sealing area can therefore be guaranteed using the present invention.

The pressure across the sealing area can also be calculated as a function of displacement using Equations 1 and 3, where the pressure P is the force F divided by the area A:

$$P = \frac{F}{\pi\left(\left(\frac{d}{d_0}(r_{max} - r_0)\right)^2 + \frac{2dr_0}{d_o}(r_{max} - r_0)\right)} \quad (5)$$

This Equation is graphically illustrated in FIG. 6 for forces F of 1200 N and 1800 N with the same cassette dimensions as FIG. 5. It can be seen from this graph that, when a 1200 N force is applied, a pressure of 100 MPa exists when displacement is 0.05 mm. When the displacement is 0.1 mm, a pressure of 44.2 MPa exists. Plastic deformation will in general stop occurring when the pressure drops below the compressive yield stress of the material. For a material such as PETG having a compressive yield stress of about 85 MPa, the final displacement d when a force of 1200 N is applied can be calculated to be 0.056 mm. Equation 3 gives a seal area A of 14.09 mm² for this displacement. Thus, when a force of 1200 N is used and the compressive yield stress of the material is 85 MPa, the second cassette part will move downwards 0.56 mm relative to the first cassette part to create a sealing area of approximately 14 mm². Larger sealing areas, and larger relative displacements, can be achieved using larger forces as can be derived from FIGS. 5 and 6. The sealing area achieved can be limited if desired by limiting the possible displacement d by proper design of the flange 262 and protrusion 214. A fixed sealing area can thus be assured even if an over-force is applied. A fixed sealing area can also be assured by providing that the whole end face 220 of the protrusion 216 deforms and relying on the abutment of the flange 262 with the first protrusion 214 to stop relative displacement of the cassette parts. In this case, the area of sealing will be equal to the area of the end face 220 when viewed in the longitudinal direction.

In the preferred embodiment, the first and second cassette parts are preferably manufactured from PETG. This material has been found to meet the following useful criteria:
- ability to form a bond with the rupturable diaphragms (which are preferably PET);
- approval for use in medical devices;
- compatibility with DNA (which may be carried on the particles);
- susceptible and stable under sterilisation by gamma irradiation; and
- moisture uptake resistance.

Other materials may nevertheless be used, preferably polymers. The following table lists possible materials together with a range for their compressive yield strength C in MPa:

| Polymer | Compressive Yield Strength, MPa |
| --- | --- |
| Acrylonitrile Butadiene Styrene (ABS) | 53-86 |
| ABS/PVC Alloy | 2.1-40 |
| Acetal Copolymer | 11-110 |
| Acetal Homopolymer | 22-124 |
| Acrylic | 100-117 |
| Acrylic, Impact Modified | 42.8-79 |
| Acrylonitrile-Methyl Acrylate Copolymer | 83 |
| Polytetrafluoroethylene (PTFE) | 10-15 |
| Fluorinated Ethylene Propylene (FEP) | 14-15.2 |
| Fluorocarbon ETFE/ECTFE | 14 |
| Polyvinylidinefluoride (PVDF) | 17-80 |
| Polychlorotrifluoroethylene | 10 |
| Polyetheretherketone | 29-150 |
| Liquid Crystal Polymer (LCP) | 60-131 |
| Nylon 6 | 10-83 |
| Nylon 46 | 23 |
| Nylon 66 | 11-100 |
| Nylon 610 | 69 |
| Nylon 612 | 16.5-69 |
| Nylon 11 | 69 |
| Nylon 12 | 13 |
| Polyamide-Imide | 27-240 |
| Polyarylate | 60 |
| Polybenzimidazole | 42-345 |
| Polycarbonate | 18-86 |
| Polydicyclopentadiene | 58 |
| Polybutylene Terephthalate (PBT), | 43.1-79 |
| Polyethylene Terephthalate (PET), | 90 |
| Copolyester (PETG) | 85 (estimate) |
| Polyetherimide | 25-152 |
| Polyethersulfone (PES) | 97-103 |
| High Density Polyethylene (HDPE) | 4-25 |
| Polymethylpentene | 23 |
| Polyphenylene Sulfide (PPS); | 28-125 |
| Polypropylene | 47-50 |
| Polystyrene | 90 |
| Styrene Acrylonitrile (SAN) | 70-150 |
| Styrene-Maleic Anhydride (SMA) | |
| Thermoplastic Polyurethane | |
| Polysulfone | 20-97 |
| Polyphenylsulfone | 18-92 |
| Polyarylsulfone | 100-120 |
| PVC | 50-56 |
| PVC/Polypropylene Alloy | 70 |
| PVC/Acrylic Alloy | |

It will be appreciated that the particular compressive yield strength will be selected in conjunction with selection of the cassette dimensions and with selection of a predetermined minimum force so as to ensure a certain sealing area between the cassette parts. When materials having lower compressive yield strengths are used, smaller predetermined forces can be used.

Figure 7:
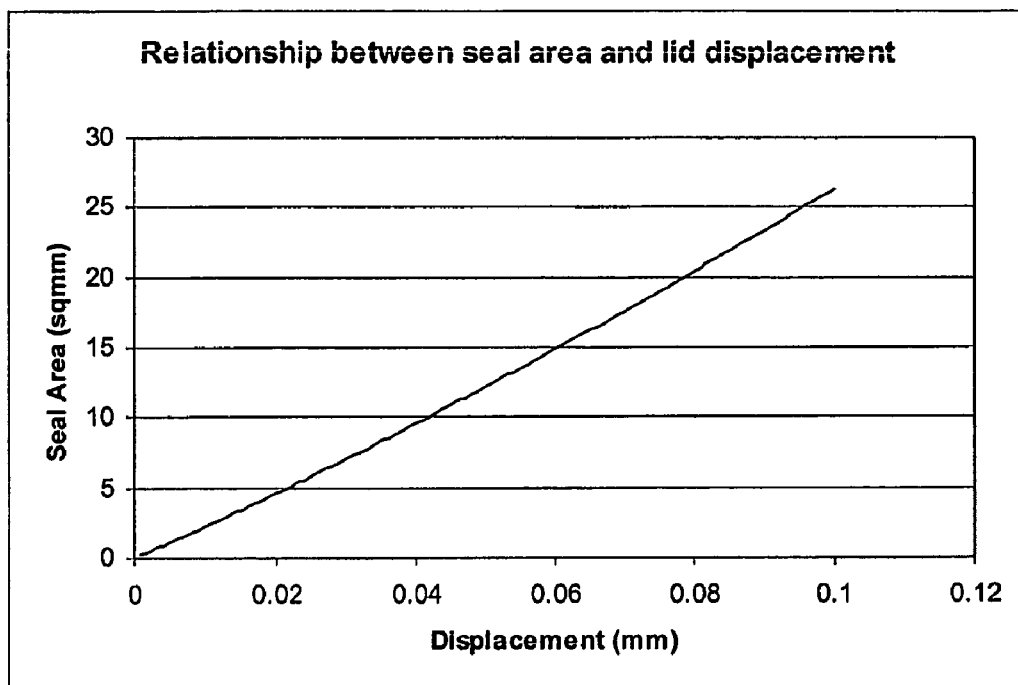
FIG. 7 is a graph showing the relationship between seal area and displacement for the particle cassette of the preferred embodiment.
Figure 8:
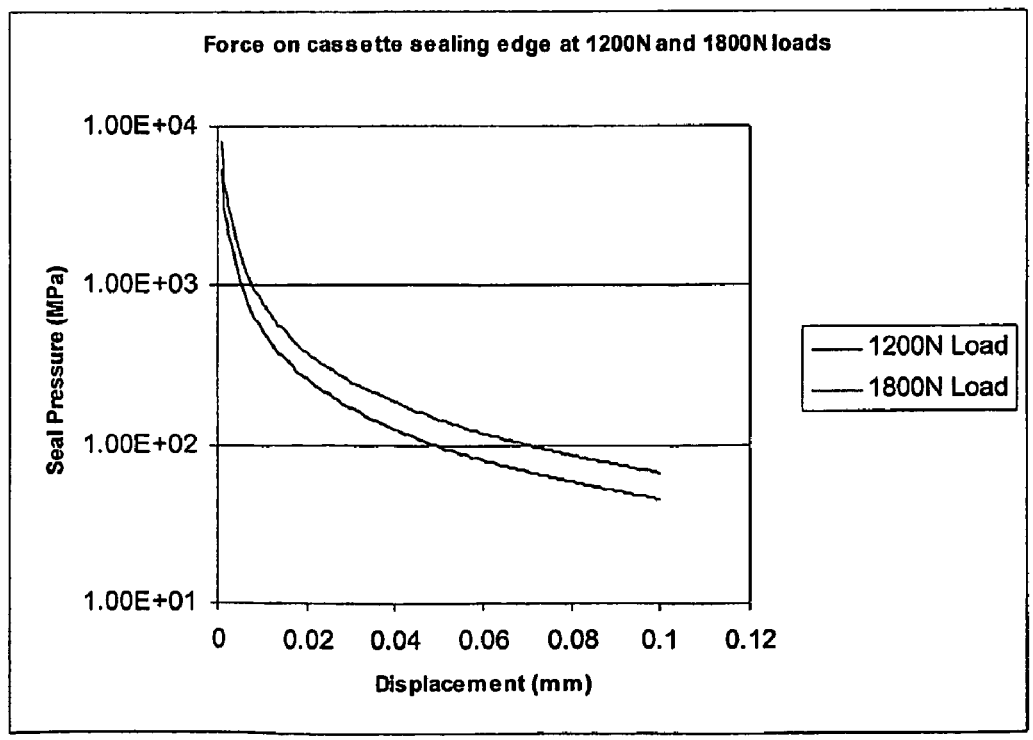
FIG. 8 is a graph showing the relationship between seal pressure and displacement for two different predetermined forces for the particle cassette of the preferred embodiment.

FIGS. 7 and 8 show exemplary apparatus for producing the assembled particle cassette. The apparatus 400 comprises a first platen 402 provided on a base substrate 406 and a second platen 404 provided on a plunger 408 attached to an air cylinder 410. The air cylinder 410 is supplied with pressurised air from an air supply and regulator 412 (which in this example also serves to support the air cylinder 410 and platen 404).

To manufacture a particle cassette, the first cassette part 210 is placed on the bottom platen 402. The particles are introduced into the chamber 218 and the second cassette part 250 is longitudinally aligned with the first cassette part. Air at a predetermined pressure is then supplied from the regulated supply 412 to the air cylinder 410 so as to move the plunger 408. The platen 404 thereafter moves downwards until it comes into contact with the second cassette part 250 and exerts a predetermined force thereon. The first and second cassette parts are thus moved together under this predetermined force so as to create a seal between the end sealing face 220 of the first cassette part and the second rupturable membrane 204. The platen 404 is thereafter moved upwardly by supplying negative air pressure to the air cylinder 410 and the assembled cassette is removed so that the device is ready to produce another cassette. This procedure can be repeated to produce a plurality of cassettes.

Particle cassettes made according to the present invention have been tested to check that a proper hermetic seal has been achieved. Cassettes manufactured according to the first embodiment and assembled using the apparatus of FIG. 9 have been placed in a measurement fixture within a vacuum chamber.

The measurement fixture has tips that locate on the external surface of the cassette's top and bottom membranes. The fixture measures the displacement of the cassette membranes.

The membrane displacement measurement is zeroed before vacuum is applied, i.e., at atmospheric pressure. The vacuum chamber is closed and a vacuum of −80 kPa is applied. The membrane displacement is noted when the vacuum first reaches −80 kPa and a countdown timer started. The membrane displacement is recorded again after 30 seconds. The cassette passes the seal integrity test if there is an initial membrane displacement when vacuum is applied and the membrane displacement is maintained over the 30 second time period.

This seal integrity test was carried out for a number of different assembly conditions. The table below summarises the results:

| Pressure (bar) On 50 mm diameter Piston | Load (N) | Time (sec) | No of cassettes studied | No. Cassettes that leaked during 30 s at −80 kPa | Mean cassette height (mm) |
|---|---|---|---|---|---|
| 9 | 1767 | 4 | 30 | 0 | 6.920 |
| 9 | 1767 | 2 | 30 | 0 | 6.919 |
| 8 | 1571 | 4 | 10 | 0 | 6.997 |
| 8 | 1571 | 3.5 | 10 | 0 | 6.994 |
| 8 | 1571 | 3 | 10 | 1 | 6.995 |
| 8 | 1571 | 2.5 | 10 | 0 | 6.999 |
| 8 | 1571 | 2 | 10 | 1 | 7.005 |
| 8 | 1571 | 1 | 10 | 7 | 7.005 |
| 8 | 1571 | 0.5 | 10 | 9 | 7.013 |
| 7.5 | 1473 | 1 | 10 | 8 | 7.013 |
| 7.5 | 1473 | 2 | 10 | 1 | 7.007 |
| 7 | 1374 | 2 | 10 | 2 | 7.003 |

The pressure in the first column is the pressure applied to a 50 mm diameter piston in the apparatus of FIG. 9. The actual load in Newtons is calculated and shown in the second column. The dwell time for which the load is applied is given in the third column and the number of cassettes studied for each set of operating parameters is given in the fourth column. The fifth column gives the number of cassettes that did not pass the seal integrity test. The sixth column gives the total height of the assembled particle cassette after assembly. This is a measure of the size of the seal that has been achieved—due to the taper, a smaller total height means a larger seal area.

It will be appreciated from the table that, in general, if the force used to compress the cassette parts is increased, the dwell time necessary to ensure a consistent seal can be reduced. With a force of 1767 N, a dwell time of 2 seconds was sufficient to ensure that all 30 cassettes studied passed the seal integrity test. However, with a force of 1374 N and a dwell time of 2 seconds, 20% of the cassettes did not pass the seal integrity test. When very short dwell times are used with moderate forces, for example 0.5 to 1 second, most cassettes fail the seal integrity test but it is expected that shorter dwell times can be used with larger forces and still provide reliable cassette sealing.

The invention has been described with reference to a particle cassette design that is generally circular when viewed in the longitudinal direction. Thus, use has been made of the terms "radius", "diameter", "annular", etc. The invention is equally applicable to non-circular cassette variations and these terms are to be interpreted accordingly. For example, the particle cassette may have a square or rectangular configuration when viewed in the longitudinal direction in which case the protrusions 214, 216 may not necessarily be circular as illustrated but maybe square or rectangular.

The invention claimed is:

1. A method of producing a particle cassette for a needleless syringe device, said method comprising the steps of:
   (a) providing a first cassette part having a first rupturable membrane bonded thereto;
   (b) providing a second cassette part having a second rupturable membrane bonded thereto;
   (c) aligning said first and second parts longitudinally;
   (d) applying a predetermined force in the longitudinal direction so as to push the first and second cassette parts together to cause plastic deformation of a part of said cassette so as to create a hermetically sealed chamber between said first rupturable membrane and said second rupturable membrane,
   wherein said predetermined force applied in step (d) is chosen according to either of the following formulas:

$F \ni 0.1 CA_{max}$ or $F \ni 2C$ wherein F is the predetermined force in Newtons, C is the compressive yield strength of the portion that plastically deforms in MPa and $A_{max}$ is the maximum possible sealing area achievable with the cassette parts in mm$^2$.

2. A method according to claim 1, wherein said plastic deformation is of a cassette part other than a membrane.

3. A method according to claim 2, wherein said part that plastically deforms comprises a sealing end face and said plastic deformation is plastic deformation of said sealing end face.

4. A method according to claim 3, wherein said sealing end face is tapered and said plastic deformation is such as to deform the taper so as to become at least partially planar in a plane perpendicular to the longitudinal direction.

5. A method according to claim 4, wherein said first cassette part comprises said sealing end face and said sealing end face is sealed directly against said second rupturable membrane of said second cassette part.

6. A method according to claim 5, wherein said sealing end face is located on a protrusion of said first cassette part.

7. A method according to claim 6, wherein said protrusion is an annular protrusion.

8. A method according to claim 4, wherein the first cassette part is made of PETG and comprises the sealing end face and the sealing end face is located on an annular protrusion of the first cassette part and the sealing end face is sealed directly against the second rupturable membrane of the second cassette part wherein the second rupturable membrane is made of PET.

9. A method according to claim 8 further comprising, after step (b), providing particles to said first cassette part adjacent said first rupturable membrane such that said particles are thereafter contained in said hermetically sealed chamber created in step (d).

10. The method according to claim 9 wherein the first and second cassette parts are moved closer together longitudinally during step (d) by no more than 0.1 mm and wherein the predetermined force is applied by compressing the first and second cassette parts together using platens and wherein said predetermined force applied in step (d) is greater than 200 N and the predetermined force is held for a predetermined dwell time of 0.1 to 10 seconds.

11. A method according to claim 2, further comprising, after step (b), providing particles to said first cassette part adjacent said first rupturable membrane such that said particles are thereafter contained in said hermetically sealed chamber created in step (d).

12. A method according to claim 11, wherein said first cassette part is made of PETG and said second rupturable membrane is made of PET.

13. A method according to claim 1 or 2, wherein said plastic deformation is of said first cassette part or of a third cassette part.

14. A method according to claim 1, wherein said first and second cassette parts are moved closer together longitudinally during step (d).

15. A method according to claim 14, wherein said first and second cassette parts are moved closer together by no more than 0.1 mm.

16. A method according to claim 1, wherein the compressive yield strength of the portion that plastically deforms lies in the range 50 MPa to 100 MPa.

17. A method according to claim 1, wherein the compressive yield strength of the second rupturable membrane is greater than the compressive yield strength of the portion of the first cassette part that plastically deforms.

18. A method according to claim 1, wherein said predetermined force is applied by compressing the first and second cassette parts together using platens.

19. A method according to claim 1, wherein said predetermined force is held for a predetermined dwell time.

20. A method according to claim 19, wherein said dwell time is 0.1 to 10 seconds.

* * * * *

UNITED STATES PATENT AND TRADEMARK OFFICE
CERTIFICATE OF CORRECTION

PATENT NO. : 8,298,173 B2  Page 1 of 1
APPLICATION NO. : 12/303885
DATED : October 30, 2012
INVENTOR(S) : Nigel Robert Bates et al.

It is certified that error appears in the above-identified patent and that said Letters Patent is hereby corrected as shown below:

IN THE CLAIMS:

Column 14, Claim 1, line 18: replace "$F \not\geq 0.1 CA_{max}$ or $F \not\geq 2C$" with -- $F \geq 0.1\ CA_{max}$ or $F \geq 2C$ --

Signed and Sealed this
Nineteenth Day of March, 2013

Teresa Stanek Rea
*Acting Director of the United States Patent and Trademark Office*